United States Patent [19]

Waterbury

[11] 4,402,967
[45] Sep. 6, 1983

[54] METHOD FOR LOWERING INTRAOCULAR PRESSURE

[75] Inventor: L. David Waterbury, Cupertino, Calif.

[73] Assignee: Syntex (U.S.A.) Inc., Palo Alto, Calif.

[21] Appl. No.: 256,623

[22] Filed: Apr. 23, 1981

[51] Int. Cl.³ ............................................ A61K 31/415
[52] U.S. Cl. .............................. 424/273 R; 424/273 B
[58] Field of Search ........................ 424/273 R, 273 B

[56] References Cited

U.S. PATENT DOCUMENTS

| | | | |
|---|---|---|---|
| 2,979,511 | 4/1961 | Krapcho et al. | 260/309.6 |
| 3,360,529 | 12/1967 | Smith-Kline | 260/340.3 |
| 3,829,411 | 8/1974 | Smith-Kline | 260/158 |
| 3,829,441 | 8/1974 | Gardner | 260/340.3 |
| 3,944,549 | 3/1976 | Lafon | 544/295 |
| 3,959,283 | 5/1976 | Lafon | 424/250 |
| 4,301,171 | 11/1981 | Kluge et al. | 424/273 B |
| 4,302,469 | 11/1981 | Kluge et al. | 424/273 R |
| 4,315,021 | 2/1982 | Kluge et al. | 424/273 R |

FOREIGN PATENT DOCUMENTS

| | | |
|---|---|---|
| 643853 | 8/1964 | Belgium . |
| 837386 | 5/1976 | Belgium . |
| 731147 | 3/1966 | Canada . |
| 54-103893 | 8/1979 | Japan . |
| 55-15455 | 2/1980 | Japan . |
| 55-15456 | 2/1980 | Japan . |
| 730718 | 12/1973 | Netherlands . |
| 641622 | 7/1964 | South Africa . |
| 1051143 | 12/1966 | United Kingdom . |
| 1094982 | 12/1967 | United Kingdom . |

Primary Examiner—Douglas W. Robinson
Attorney, Agent, or Firm—Hana Dolezalova; Tom M. Moran; Alan M. Krubiner

[57] ABSTRACT

Methods of and compositions for lowering intraocular pressure using compounds of the formula

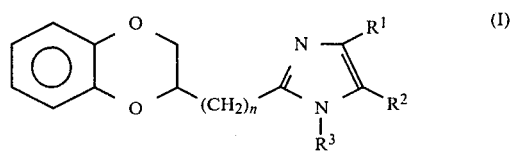

wherein $R^1$ and $R^2$ are each independently selected from the group consisting of hydrogen, lower alkyl, optionally substituted phenyl, and optionally substituted phenyl lower alkyl; or wherein $R^1$ and $R^2$ taken together form an optionally substituted benzo;

$R^3$ is hydrogen, alkyl, or optionally substituted phenyl lower alkyl;

n is an integer equal to 0, 1 or 2; and the pharmaceutically acceptable acid addition salts thereof, are disclosed.

8 Claims, No Drawings

METHOD FOR LOWERING INTRAOCULAR PRESSURE

BACKGROUND OF THE INVENTION

Degenerative diseases of the eye are widespread among middle aged and elderly people. The most common of these diseases is glaucoma. A variety of topically applied medicinal compounds have been used to treat this disorder, although none is completely satisfactory. A class of compounds containing a benzodioxanyl moiety attached through an alkyl chain to an imidazole ring have now been found to be useful in the treatment of this disorder by the lowering of intraocular pressure. Compounds having the structures which disclosed as useful in lowering intraocular pressure herein previously have been described as $\alpha_2$ blocking agents in U.S. Pat. Nos. 4,301,171, 4,302,468 and 4,315,021.

SUMMARY OF THE INVENTION

The present invention concerns methods for lowering the intraocular pressure in the eye and of treating eye disorders in mammalian subjects using a compound of the formula

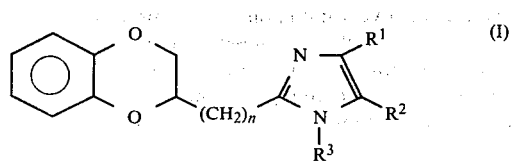

or its pharmaceutically acceptable acid addition salts wherein $R^1$ and $R^2$ are each independently selected from the group consisting of hydrogen, lower alkyl, optionally substituted phenyl, and optionally substituted phenyl lower alkyl; or wherein $R^1$ and $R^2$ taken together form an optionally substituted benzo;

$R^3$ is hydrogen, alkyl, or optionally substituted phenyl lower alkyl;

n is an integer equal to 0, 1 or 2.

In further aspects, the invention concerns topical compositions for treating disorders of the eye and for intraocular-pressure lowering containing compounds of formula I and its pharmaceutically acceptable acid addition salts.

DETAILED DESCRIPTION OF THE INVENTION

Definitions

As used herein

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicyclic acid and the like.

"lower alkyl" means a branched or unbranched saturated hydrocarbon chain of 1-4 carbons, such as, for example, methyl, ethyl, n-propyl, i-butyl and the like.

"Alkoxy" means the group —OR wherein R is alkyl as herein defined.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

"Substituted phenyl" as used herein means that one or more hydrogens of the phenyl ring are replaced by identical moieties selected from the group consisting of lower alkyl, halo, and trifluoromethyl. In the context of the present invention, said replacement may be at any available position of the phenyl ring, and a maximum of 3 hydrogens may be so replaced.

"Substituted benzo" means that one or two hydrogens of the free position on the benzene ring (herein fused to the imidazole) are replaced by identical moieties selected from the group consisting of lower alkyl, halo, and trifluoromethyl.

"Optionally substituted phenyl lower alkyl" means a moiety in which the phenyl, which may or may not be substituted as described above, is attached to the imidazole ring of the compounds of this invention by an intervening lower alkyl. Such embodiments of "optionally substituted phenyl lower alkyl", are, for example benzyl, phenylethyl, 2-(4-fluorophenyl)ethyl 3-(3,5-dimethylphenyl)-n-propyl and the like.

Utility and Administration

The compounds of formula I and their pharmaceutically acceptable acid addition salts have been found, in animal experiments, to lower intraocular pressure. Accordingly, these compounds offer a method for treating disorders of the eye in mammals which are associated with increased intraocular pressure.

In the practice of the invention, the compounds of formula I or their pharmaceutically acceptable acid addition salts are administered topically to a subject requiring diminution of intraocular pressure. Administration is in the form of drops or a solution applied directly to the eye.

Such compositions are typically sterilized aqueous solutions (i.e. eyedrops) containing 0.001% to 10% wt/vol most preferably 0.005% to 1% of the active ingredient, along with suitable buffer, stabilizer, and preservative. The total concentration of solutes should be such that, if possible, the resulting solution is isotonic with the lacrimal fluid (though this is not absolutely necessary) and has an equivalent pH in the range of pH 6-8. Typical preservatives/sterilants are phenyl mercuric acetate, thimerosal, chlorobutanol, and benzalkonium chloride. Typical buffer systems and salts are based on, for example, citrate, borate or phosphate; suitable stabilizers include glycerin and polysorbate 80. The aqueous solutions are formulated simply by solutes in a suitable quantity of water, adjusting the pH to about 6.8-8.0, making a final volume adjustment with additional water, and sterilizing the preparation using methods known to those in the art.

The dosage level of the resulting composition will, of course, depend on the concentration of the drops, the condition of the subject and the individual magnitude of reponses to treatment. However, typical dosage ranges might be about 2–10 drops of a 0.1% solution of active ingredient per day.

Preferred Embodiments

A preferred embodiment of the present invention is that wherein the compound of formula I is selected from the group consisting of compounds wherein $R^1$, $R^2$ and $R^3$ are each independently hydrogen, lower alkyl, and optionally substituted phenyl lower alkyl, and the pharmaceutically acceptable acid addition salts thereof. Still more preferred are those embodiments wherein the compound of formula I is selected from the group consisting of compounds wherein $R^1$ and $R^2$ are hydrogen or, together unsubstituted benzo, $R^3$ is lower alkyl or benzyl and the pharmaceutically acceptable acid addition salts thereof. Still more preferred are those embodiments wherein the compound of formula I is selected from the group consisting of
2-benzodioxan-2-ylimidazole
2-(benzodioxan-2-yl)methyl imidazole
2-(2-(benzodioxan-2-yl)ethyl imidazole
1-ethyl-2-benzodioxan-2-ylimidazole
1-ethyl-2-(benzodioxan-2-yl)methyl imidazole
1-ethyl-2-(2-(benzodioxan-2-yl)ethyl imidazole
1-benzyl-2-benzodioxan-2-ylimidazole
1-benzyl-2-(benzodioxan-2-yl)methyl imidazole
1-benzyl-2-(2-(benzodioxan-2-yl)ethyl imidazole,
and their pharmaceutically acceptable acid addition salts.

The following examples are intended to illustrate, but not to limit, the scope of the invention.

EXAMPLE 1

Composition for Topical Administration to the Eye

The composition contains:

|  | % wt/vol |
|---|---|
| Active ingredient | 0.10 |
| Benzalkonium chloride | 0.02 |
| EDTA | 0.01 |
| Phenylethanol | 0.25 |
| Boric acid | 1.62 |
| NaOH | to adjust pH |
| water qs ad | 100 ml |

The active ingredient in this example is 2-(benzodioxan-2-yl)methyl imidazole, but other compounds of this invention may be substituted therefor.

The first five ingredients are dissolved in less than the required total volume of water, and the pH adjusted to 7.4. The volume is then brought to 100 ml with additional water.

EXAMPLE 2

Determination of Effect on Intraoccular Pressure

Protocol:

The compound to be tested is dissolved in saline, and applied topically to the eye. The intraocular pressure is measured immediately before application, and at specified time intervals thereafter, by means of a probe which measures the force necessary to flatten a small area or corneal surface, according to the method described by Moses, R. A., *Tr. Am. Acad. Opth. and Otol.*, January–February 1962: 88–95. Results are expressed in torr (mm Hg).

Results:

A 0.1% solution of 2-(1,4-benzodioxan-2-ylmethyl)imidazole was applied to the right and left eyes of New Zealand white rabbits and the following pressure readings were obtained.

|  | No. Rabbits | Average Pressure | | | |
|---|---|---|---|---|---|
|  |  | Initial | 2 hr | 4 hr | 6 hr |
| Expt 1 | 6 | 18.3 | 15.3 | — | — |
| Expt 2 | 6 | 18.0 | 16.1 | 16.5 | 18.0 |

We claim:
1. A method for lowering intraocular pressure in the mammalian eye which comprises administering directly to the eye of a subject in need of such treatment a therapeutically effective amount of, or a pharmaceutical composition containing a therapeutically effective amount of, a compound of the formula

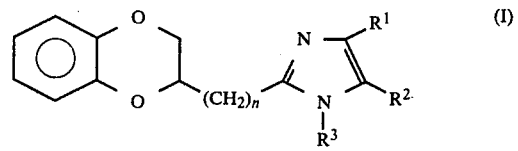

wherein
$R^1$ and $R^2$ are each independently selected from the group consisting of hydrogen, lower alkyl, optionally substituted phenyl, and optionally substituted phenyl lower alkyl; or wherein $R^1$ and $R^2$ taken together form an optionally substituted benzo;
$R^3$ is hydrogen, alkyl, or optionally substituted phenyl lower alkyl;
n is an integer equal to 0, 1 or 2; or a pharmaceutically acceptable acid addition salt thereof.

2. The method of claim 1 wherein the compound of formula I is selected from the group consisting of compounds wherein $R^1$, $R^2$ and $R^3$ are each independently hydrogen, lower alkyl, and optionally substituted phenyl lower alkyl, and the pharmaceutically acceptable acid addition salts thereof.

3. The method of claim 1 wherein the compound of formula I is selected from the group consisting of compounds wherein $R^1$ and $R^2$ are hydrogen or, together are unsubstituted benzo, $R^3$ is lower alkyl or benzyl and the pharmaceutically acceptable acid addition salts thereof.

4. The method of claim 1 wherein the compound of formula I is selected from the group consisting of
2-benzodioxan-2-ylimidazole
2-(benzodioxan-2-yl)methyl imidazole
2-(2-(benzodioxan-2-yl)ethyl imidazole 1-ethyl-2-benzodioxan-2-ylimidazole
1-ethyl-2-(benzodioxan-2-yl)methyl imidazole
1-ethyl-2-(2-(benzodioxan-2-yl)ethyl imidazole
1-benzyl-2-benzodioxan-2-ylimidazole
1-benzyl-2-(benzodioxan-2-yl)methyl imidazole
1-benzyl-2-(2-benzodioxan-2-yl)ethyl imidazole,
and their pharmaceutically acceptable acid addition salts.

5. A topical pharmaceutical composition for lowering intraocular pressure in the mammalian eye which comprises an intraocular pressure lowering amount of a compound of the formula

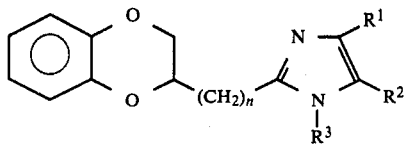

wherein
$R^1$ and $R^2$ are each independently selected from the group consisting of hydrogen, lower alkyl, optionally substituted phenyl, and optionally substituted phenyl lower alkyl; or wherein $R^1$ and $R^2$ taken together form an optionally substituted benzo;
$R^3$ is hydrogen, alkyl, or optionally substituted phenyl lower alkyl;
n is an integer equal to 0, 1 or 2; or a pharmaceutically acceptable acid addition salt thereof in admixture with at least one pharmaceutically acceptable topical excipient.

6. The composition of claim 5 wherein the compound of formula I is selected from the group consisting of compounds wherein $R^1$, $R^2$ and $R^3$ are each independently hydrogen, lower alkyl, and optionally substituted phenyl lower alkyl, and the pharmaceutically acceptable acid addition salts thereof.

7. The composition of claim 5 wherein the compound of formula I is selected from the group consisting of compounds wherein $R^1$ and $R^2$ are hydrogen or, together are unsubstituted benzo, $R^3$ is lower alkyl or benzyl and the pharmaceutically acceptable acid addition salts thereof.

8. The composition of claim 5 wherein the compound of formula I is selected from the group consisting of
2-benzodioxan-2-ylimidazole
2-(benzodioxan-2-yl)methyl imidazole
2-(2-(benzodioxan-2-yl)ethyl imidazole
1-ethyl-2-benzodioxan-2-ylimidazole
1-ethyl-2-(benzodioxan-2-yl)methyl imidazole
1-ethyl-2-(2-(benzodioxan-2-yl)ethyl imidazole
1-benzyl-2-benzodioxan-2-ylimidazole
1-benzyl-2-(benzodioxan-2-yl)methyl imidazole
1-benzyl-2-(2-(benzodioxan-2-yl)ethyl imidazole,
and their pharmaceutically acceptable acid addition salts.

* * * * *